(12) United States Patent
Muir

(10) Patent No.: US 7,618,467 B2
(45) Date of Patent: Nov. 17, 2009

(54) DETERGENT / ANTI-OXIDANT ADDITIVES FOR FUELS AND LUBRICANTS

(75) Inventor: Ronald J. Muir, West Hill (CA)

(73) Assignee: Chemtura Corporation, Middlebury, CT (US)

( * ) Notice: Subject to any disclaimer, the term of this patent is extended or adjusted under 35 U.S.C. 154(b) by 855 days.

(21) Appl. No.: 11/037,623

(22) Filed: Jan. 17, 2005

(65) Prior Publication Data

US 2005/0172543 A1 Aug. 11, 2005

Related U.S. Application Data

(60) Provisional application No. 60/539,590, filed on Jan. 29, 2004.

(51) Int. Cl.
*C10M 163/00* (2006.01)
*C10M 139/00* (2006.01)
*C10L 1/22* (2006.01)

(52) U.S. Cl. .................. 44/317; 508/185; 508/189; 508/190; 44/314

(58) Field of Classification Search .......... 44/314, 44/317; 585/185, 189–190
See application file for complete search history.

(56) References Cited

U.S. PATENT DOCUMENTS

| | | | |
|---|---|---|---|
| 2,933,520 A | 4/1960 | Bader | 260/473 |
| 3,038,935 A | 6/1962 | Gerber et al. | 260/520 |
| 3,133,944 A | 5/1964 | Christenson | 260/434 |
| 3,189,652 A | 6/1965 | Pollitzer | 260/584 |
| 3,239,463 A | 3/1966 | Knowles et al. | |
| 3,446,808 A | 5/1969 | Cyba | 260/250 |
| 3,471,537 A | 10/1969 | Berke et al. | 260/429 |
| 3,505,226 A | 4/1970 | Cyba | |
| 3,673,186 A | 6/1972 | Cyba | 260/268 |
| 3,692,680 A | 9/1972 | Cyba | 252/49.6 |
| 3,787,416 A | 1/1974 | Cyba | 260/251 |
| 3,914,182 A | 10/1975 | Ker et al. | |
| 4,474,670 A | 10/1984 | Braid et al. | |
| 4,529,528 A | 7/1985 | Horodysky | |
| 4,533,481 A | 8/1985 | Jahnke | |
| 4,741,848 A | 5/1988 | Koch et al. | |
| 4,828,733 A | 5/1989 | Farng et al. | 252/42.7 |
| 4,906,252 A | 3/1990 | Gutierrez et al. | |
| 5,023,366 A | 6/1991 | Yamaguchi et al. | 560/71 |
| 5,110,488 A | 5/1992 | Tipton et al. | |
| 5,281,346 A | 1/1994 | Adams et al. | 252/38 |
| 5,330,666 A | 7/1994 | Habeeb | 252/34 |
| 5,336,278 A | 8/1994 | Adams et al. | 44/419 |
| 5,356,546 A | 10/1994 | Blystone et al. | 252/35 |
| 5,458,793 A | 10/1995 | Adams et al. | 252/48 |
| 5,498,809 A | 3/1996 | Emert et al. | 585/13 |
| 5,523,431 A | 6/1996 | Skold | |
| 5,688,751 A | 11/1997 | Cleveland et al. | 508/518 |
| 5,698,499 A | 12/1997 | Baranski et al. | |
| 5,854,182 A | 12/1998 | Swami et al. | 508/186 |
| 5,900,392 A * | 5/1999 | Bernhard | 508/154 |
| 6,174,842 B1 | 1/2001 | Gatto et al. | 508/364 |
| 6,191,330 B1 * | 2/2001 | Matsuno et al. | 585/21 |
| 6,200,936 B1 | 3/2001 | Moreton | 508/479 |
| 6,242,393 B1 * | 6/2001 | Ishida et al. | 508/462 |
| 6,268,320 B1 | 7/2001 | Crawford | 508/572 |
| 6,310,011 B1 | 10/2001 | Karn et al. | 508/460 |
| 6,339,052 B1 | 1/2002 | Dohhen et al. | 508/436 |
| 6,355,074 B1 * | 3/2002 | Emert et al. | 44/317 |
| 2003/0000866 A1 | 1/2003 | Cain | |
| 2004/0038834 A1 | 2/2004 | Gahagan | |
| 2006/0276350 A1 | 12/2006 | Habeeb et al. | |
| 2006/0281643 A1 | 12/2006 | Habeeb et al. | |

FOREIGN PATENT DOCUMENTS

| | | |
|---|---|---|
| JP | 08165484 A | 6/1996 |
| WO | 0949321 A2 | 10/1999 |
| WO | WO 2004104146 A1 | 12/2004 |
| WO | 2005/073352 A1 | 8/2005 |
| WO | WO2008016485 | 2/2008 |

OTHER PUBLICATIONS

Lubrication and Lubricants, E.R. Braithwaite. Ed., Elsevier Co. (N.Y. 1967), Chapter 166-196, Synthetic Lubricants.
J.A. Walker et al., Characterization of Lubrication Oils by Differential Scanning Ca SAE Technical Paper Series, 801383, pp. 20-23. 1980.
USPTO Office Action mailed Apr. 28, 2009 ; U.S. Appl. No. 12/333,938; 32 Pgs.
USPTO Office Action mailed Apr. 2, 2009 ; U.S. Appl. No. 12/334,065; 25 Pgs.
Response filed Jun. 30, 2009, to USPTO Office Action mailed Apr. 2, 2009; U.S. Appl. No. 12/334,065; 10 Pgs.
USPTO Office Action mailed Apr. 2, 2009 ; U.S. Appl. No. 12/336,076; 28 Pgs.
Response filed Jun. 30, 2009, to USPTO Office Action mailed Apr. 2, 2009; U.S. Appl. No. 12/336,076; 14 Pgs.
USPTO Office Action mailed Mar. 17, 2009 ; U.S. Appl. No. 12/336,119; 15 Pgs.
Response filed May 29, 2009, to USPTO Office Action mailed Mar. 17, 2009 ; U.S. Appl. No. 12/336,119; 13 Pgs.
USPTO Office Action mailed Apr. 29, 2008; U.S. Appl. No. 11/124,652; 10 Pgs.
Response filed Jul. 11, 2008, to USPTO Office Action mailed Apr. 29, 2008; U.S. Appl. No. 11/124,652; 13 Pgs.
USPTO Office Action mailed Oct. 17, 2008; U.S. Appl. No. 11/124,652; 8 Pgs.
Response filed Jan. 16, 2009; to USPTO Office Action mailed Oct. 17, 2008; U.S. Appl. No. 11/124,652; 13 Pgs.
USPTO Office Action mailed May 8, 2009 ; U.S. Appl. No. 11/124,652; 7 Pgs.
USPTO Office Action mailed Jan. 27, 2009; U.S. Appl. No. 11/326,282; 10 Pgs.
Response filed May 27, 2009; to USPTO Office Action mailed Oct. 17, 2008; U.S. Appl. No. 11/326,282; 10 Pgs.

* cited by examiner

*Primary Examiner*—Glenn A Caldarola
*Assistant Examiner*—Pamela Weiss
(74) *Attorney, Agent, or Firm*—Jaimes Sher

(57) ABSTRACT

A composition is disclosed that comprises the reaction product of an acidic organic compound, a boron compound, and a basic organic compound. The composition is useful as a detergent additive for lubricants and hydrocarbon fuels.

4 Claims, No Drawings

DETERGENT / ANTI-OXIDANT ADDITIVES FOR FUELS AND LUBRICANTS

I claim the benefit under Title 35, United States Code, § 120 to U.S. Provisional Application No. 60/539,590, file Jan. 29, 2004, entitled DETERGENT/ANTI-OXIDANT ADDITIVES FOR FUELS AND LUBRICANTS.

BACKGROUND OF THE INVENTION

1. Field of the Invention

This invention is related to fuels, especially hydrocarbon fuels, and lubricants, especially lubricating oils, and, more particularly, to a class of reduced ash detergent/anti-oxidant additives that are products of the reaction of acidic organic compounds, such as hydrocarbyl salicylic acids, basic organic compounds, such as organic nitrogen base compounds, particularly those comprising an N-hydroxy alkyl moiety, and boron compounds, such as boric acid.

2. Description of Related Art

Metal detergents represent a major source of ash in formulated engine oils. Alkaline earth sulfonates, phenates and salicylates are typically used in modern engine oils to provide detergency and alkaline reserve. Detergents are necessary components of engine oils for both gasoline and diesel engines. Incomplete combustion of the fuel produces soot that can lead to sludge deposits, as well as carbon and varnish deposits. In the case of diesel fuel, residual sulfur in the fuel burns in the combustion chamber to produce sulfur derived acids. These acids produce corrosion and corrosive wear in the engine, and they also accelerate the degradation of the oil. Neutral and overbased detergents are introduced into engine oils to neutralize these acidic compounds, thereby preventing the formation of harmful engine deposits and dramatically increasing engine life.

U.S. Pat. No. 5,330,666 discloses a lubricant oil composition useful for reducing friction in an internal combustion engine which comprises a lubricating oil basestock and an alkoxylated amine salt of a hydrocarbylsalicylic acid of a defined formula.

U.S. Pat. No. 5,688,751 discloses that two-stroke cycle engines can be effectively lubricated by supplying to the engine a mixture of an oil of lubricating viscosity and a hydrocarbyl-substituted hydroxyaromatic carboxylic acid or an ester, unsubstituted amide, hydrocarbyl-substituted amide, ammonium salt, hydrocarbylamine salt, or monovalent metal salt thereof in an amount suitable to reduce piston deposits in said engine. The mixture supplied to the engine contains less than 0.06 percent by weight of divalent metals.

U.S. Pat. No. 5,854,182 discloses the preparation of magnesium borate overbased metallic detergent having magnesium borate uniformally dispersed in an extremely fine particle size by using magnesium alkoxide and boric acid. The preparation involves reacting a neutral sulphonate of an alkaline earth metal with magnesium alkoxide and boric acid under anhydrous conditions in the presence of a dilution solvent followed by distillation to remove alcohol and part of dilution solvent therefrom. The borated mixture is then cooled, filtered to recover magnesium borated metal detergent, which is said to exhibit excellent cleaning and dispersing performance, very good hydrolytic and oxidation stability, and good extreme pressure and antiwear properties.

U.S. Pat. No. 6,174,842 discloses a lubricating oil composition that contains from about 50 to 1000 parts per million of molybdenum from a molybdenum compound that is oil-soluble and substantially free of reactive sulfur, about 1,000 to 20,000 parts per million of a diarylamine, and about 2,000 to 40,000 parts per million of a phenate. This combination of ingredients is said to provide improved oxidation control and improved deposit control to the lubricating oil.

U.S. Pat. No. 6,339,052 discloses a lubricating oil composition for gasoline and diesel internal combustion engines includes a major portion of an oil of lubricating viscosity; from 0.1 to 20.0% w/w of a component A, which is a sulfurized, overbased calcium phenate detergent derived from distilled, hydrogenated cashew nut shell liquid; and from 0.1 to 10.0% w/w of a component B, which is an amine salt of phosphorodithioic acid of a specified formula derived from cashew nut shell liquid.

The disclosures of the foregoing are incorporated herein by reference in their entirety.

SUMMARY OF THE INVENTION

According to the present invention, metal-free detergents and anti-oxidants are prepared by reacting an acidic organic compound, a boron compound, and a basic organic compound.

Preferably, the acidic organic compound is selected from the group consisting of alkyl substituted salicylic acids, di-substituted salicylic acids, oil soluble hydroxy carboxylic acids, salicylic acid calixarenes, sulfur-containing calixarenes, and the acidic structures disclosed in U.S. Pat. Nos. 2,933,520; 3,038,935; 3,133,944; 3,471,537; 4,828,733; 6,310,011; 5,281,346; 5,336,278; 5,356,546; and 5,458,793.

Preferably, the basic organic compound is an organic nitrogen base compound, such as one comprising an N-hydroxy alkyl moiety, preferably an N-hydroxy or alkoxy alkyl heterocycle, such as N-hydroxy alkyl imidazolines, N-alkoxy alkyl imidazolines, or N-hydroxy alkyl piperazines. Other heterocyclics can be pyrrolidine, piperidine, imidazolidine, pyrazolidine, and derivatives of indole, carbazole, quinoline, and the like. Oil soluble and water soluble alkanolamines, including polymeric alkanolamines, such as those described in U.S. Pat. No. 3,692,680 can also be used.

The boron compound can, for example, be boric acid, a trialkyl borate in which the alkyl groups preferably comprise from 1 to 4 carbon atoms each, alkyl boric acid, dialkyl boric acid, boric oxide, boric acid complex, cycloalkyl boric acid, aryl boric acid, dicycloalkyl boric acid, diaryl boric acid, or substitution products of these with alkoxy, alkyl, and/or alkyl groups, and the like.

The reaction product provides excellent detergency and cleanliness to an oil when evaluated using the panel coker test and excellent antioxidant performance when evaluated using pressure differential scanning calorimetry (PDSC).

More particularly, the present invention is directed to a composition comprising the reaction product of an acidic organic compound, a boron compound, and a basic organic compound.

In another aspect, the present invention is directed to a composition comprising:

(A) a lubricant, and (B) at least one reaction product of an acidic organic compound, a boron compound, and a basic organic compound.

In still another aspect, the present invention is directed to a composition comprising:

(A) a hydrocarbon fuel, and (B) at least one reaction product of an acidic organic compound, a boron compound, and a basic organic compound.

In yet another aspect, the present invention is directed to a method for reducing the formation of deposits in an internal combustion engine which comprises operating the engine with a lubricating oil containing the reaction product of an acidic organic compound, a boron compound, and a basic organic compound in an amount effective to reduce the friction.

DESCRIPTION OF THE PREFERRED EMBODIMENTS

This invention relates to lubricant or fuel compositions, especially lubricant compositions, comprising an additive comprising boron, which provides improved detergency and oxidation stability in an internal combustion engine oil. The lubricant composition comprises (a) a major amount of a lubricant, e.g., lubricating oil and (b) a minor amount of an additive that is the reaction product of an acidic organic compound, a basic organic compound, and a boron compound.

The Acidic Organic Compounds

The acidic organic compounds employed in the practice of the present invention include, but are not limited to, alkyl substituted salicylic acids, di-substituted salicylic acids, oil soluble hydroxy carboxylic acids, salicylic acid calixarenes, sulfur-containing calixarenes, and the acidic structures disclosed in U.S. Pat. Nos. 2,933,520; 3,038,935; 3,133,944; 3,471,537; 4,828,733; 6,310,011; 5,281,346; 5,336,278; 5,356,546; and 5,458,793.

The substituted salicylic acids employed in the practice of the present invention are commercially available or may be prepared by methods known in the art, e.g., U.S. Pat. No. 5,023,366. These salicylic acids are of the formula:

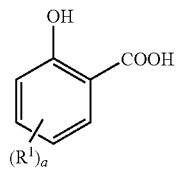

wherein $R^1$ is a hydrocarbyl group, preferably of from 1 to 30 carbon atoms, and a is an integer of 1 or 2. Where a is 2, the $R^1$ groups are independently selected, i.e., they may be the same or different.

As employed herein, the term "hydrocarbyl" includes hydrocarbon as well as substantially hydrocarbon groups. "Substantially hydrocarbon" describes groups that contain heteroatom substituents that do not alter the predominantly hydrocarbon nature of the group.

Examples of hydrocarbyl groups include the following:

(1) hydrocarbon substituents, i.e., aliphatic (e.g., alkyl or alkenyl), alicyclic (e.g., cycloalkyl, cycloalkenyl) substituents, aromatic substituents, aromatic-, aliphatic-, and alicyclic-substituted aromatic substituents, and the like, as well as cyclic substituents wherein the ring is completed through another portion of the molecule (that is, for example, any two indicated substituents may together form an alicyclic radical);

(2) substituted hydrocarbon substituents, i.e., those substituents containing non-hydrocarbon groups which, in the context of this invention, do not alter the predominantly hydrocarbon nature of the substituent; those skilled in the art will be aware of such groups (e.g., halo, hydroxy, mercapto, nitro, nitroso, sulfoxy, etc.);

(3) heteroatom substituents, i.e., substituents that will, while having a predominantly hydrocarbon character within the context of this invention, contain an atom other than carbon present in a ring or chain otherwise composed of carbon atoms (e.g., alkoxy or alkylthio). Suitable heteroatoms will be apparent to those of ordinary skill in the art and include, for example, sulfur, oxygen, nitrogen, and such substituents as, e.g., pyridyl, furyl, thienyl, imidazolyl, etc. Preferably, no more than about 2, more preferably no more than one, hetero substituent will be present for every ten carbon atoms in the hydrocarbyl group. Most preferably, there will be no such heteroatom substituents in the hydrocarbyl group, i.e., the hydrocarbyl group is purely hydrocarbon.

In the formula described above, $R^1$ is hydrocarbyl. Examples of $R^1$ include, but are not limited to, unsubstituted phenyl;

phenyl substituted with one or more alkyl groups, such as methyl, ethyl, propyl, butyl, pentyl, hexyl, heptyl, octyl, nonyl, decyl, isomers of the foregoing, and the like;

phenyl substituted with one or more alkoxy groups, such as methoxy, ethoxy, propoxy, butoxy, pentoxy, hexoxy, heptoxy, octoxy, nonoxy, decoxy, isomers of the foregoing, and the like;

phenyl substituted with one or more alkyl amino or aryl amino groups;

naphthyl and alkyl substituted naphthyl;

straight chain or branched chain alkyl or alkenyl groups containing from one to fifty carbon atoms, including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, triacontyl, pentatriacontyl, tetracontyl, pentacontyl, isomers of the foregoing, and the like; and cyclic alkyl groups, such as cyclopentyl, cyclohexyl, cycloheptyl, cyclooctyl, and cyclododecyl.

It will be noted that these salicylic acid derivatives can be either monosubstituted or disubstituted, i.e., when a in the formula equals 1 or 2, respectively.

Salicylic acid calixarenes, for example those described in U.S. Pat. No. 6,200,936, the disclosure of which is incorporated herein by reference in its entirety, can be used as the acid compounds of the present invention. Such calixarenes include, but are not limited to, cyclic compounds comprising m units of formula (Ia):

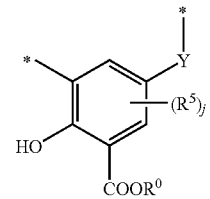

and n units of formula (Ib):

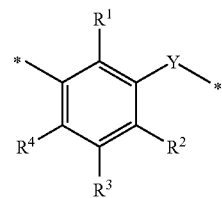

joined together to form a ring, wherein each Y is a divalent bridging group which may be the same or different in each unit; $R^0$ is H or an alkyl group of 1 to 6 carbon atoms; $R^5$ is H or an alkyl group of 1 to 60 carbon atoms; and j is 1 or 2; $R^3$ is hydrogen, a hydrocarbyl or a hetero-substituted hydrocarbyl group; either $R^1$ is hydroxy and $R^2$ and $R^4$ are independently either hydrogen, hydrocarbyl or hetero-substituted hydrocarbyl, or $R^2$ and $R^4$ are hydroxyl and $R^1$ is either hydrogen, hydrocarbyl or hetero-substituted hydrocarbyl; m is from 1 to 8; n is at least 3, and m+n is 4 to 20.

When more than one salicylic acid unit is present in the ring (i.e., m>1), the salicylic acid units (formula (Ia)) and phenol units (formula (Ib)) are distributed randomly, although this does not exclude the possibility that in some rings there may be several salicylic acid units joined together in a row.

Each Y may independently be represented by the formula $(CHR^6)_d$ in which $R^6$ is either hydrogen or hydrocarbyl and d is an integer which is at least 1. In one embodiment, $R^6$ contains 1 to 6 carbon atoms, and in one embodiment it is methyl. In one embodiment, d is from 1 to 4. Y may optionally be sulfur rather than $(CHR^6)_d$ in up to 50% of the units, such that the amount of sulfur incorporated in the molecule is up to 50 mole %. In one embodiment, the amount of sulfur is between 8 and 20 mole %, and in one embodiment the compound is sulfur-free.

For convenience, these compounds are sometimes referred to as "salixarenes" and their metal salts as "salixarates".

In one embodiment, Y is $CH_2$; $R^1$ is hydroxyl; $R^2$ and $R^4$ are independently either hydrogen, hydrocarbyl or hetero-substituted hydrocarbyl; $R^3$ is either hydrocarbyl or hetero-substituted hydrocarbyl; $R^0$ is H; $R^5$ is an alkyl group of 6 to 50 carbon atoms, preferably 4 to 40 carbon atoms, more preferably 6 to 25 carbon atoms; and m+n has a value of at least 5, preferably at least 6, more preferably at least 8, where m is 1 or 2. Preferably, m is 1.

In another embodiment, $R^2$ and $R^4$ are hydrogen; $R^3$ is hydrocarbyl, preferably alkyl of greater than 4 carbon atoms, more preferably greater than 9 carbon atoms; $R^5$ is hydrogen; m+n is from 6 to 12; and m is 1 or 2.

For a review of calixarenes, see *Monographs in Supramolecular Chemistry* by C. David Gutsche, Series Editor-J. Fraser Stoddart, published by the Royal Society of Chemistry, 1989. Calixarenes having a substituent hydroxyl group or groups include homocalixarenes, oxacalixarenes, homooxacalixarenes, and heterocalixarenes.

Sulfur-containing calixarenes, for example those described in U.S. Pat. No. 6,268,320, the disclosure of which is incorporated herein by reference in its entirety, can also be used as the acid compounds of the present invention. Such calixarenes include, but are not limited to, compounds represented by formula (II):

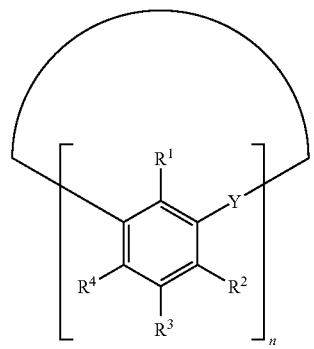

wherein in formula (II): Y is a divalent bridging group, at least one of said bridging groups being a sulfur atom; $R^3$ is hydrogen or a hydrocarbyl group; either $R^1$ is hydroxyl and $R^2$ and $R^4$ are independently either hydrogen or hydrocarbyl, or $R^2$ and $R^4$ are hydroxyl and $R^1$ is either hydrogen or hydrocarbyl; and n is a number having a value of at least 4.

In formula (II), Y is a divalent bridging group or a sulfur atom with the proviso that at least one Y group is a sulfur atom. The divalent bridging group, when not a sulfur atom, can be a divalent hydrocarbon group or divalent hetero-substituted hydrocarbon group of 1 to 18 carbon atoms, and in a preferred embodiment, 1 to 6 carbon atoms. The heteroatoms can be —O—, —NH—, or —S—. n is an integer that typically has a value of at least 4, preferably from 4 to 12, more preferably, 4 to 8. In one embodiment, n-2 to n-6 of the Y groups are sulfur atoms, in another embodiment n-3 to n-10 of the Y groups are sulfur atoms, and in a third embodiment, one of the Y groups is a sulfur atom. Preferably, the amount of sulfur incorporated in the calixarene is between 5 and 50 mole %, such that between 5 and 50% of the groups Y in formula (II) are sulfur atoms. More preferably, the amount of sulfur is between 8 and 20 mole %.

In one embodiment, when Y is not a sulfur atom, it is a divalent group represented by the formula $(CHR^6)_d$ in which $R^6$ is either hydrogen or a hydrocarbyl group and d is an integer that is at least one. $R^6$ is preferably a hydrocarbyl group group of 1 to 18 carbon atoms, more preferably, 1 to 6 carbon atoms. Examples include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, isomers or the foregoing, and the like. Preferably, d is from 1 to 3, more preferably 1 to 2, and most preferably, d is 1. As defined above, the term "hydrocarbyl groups" includes hetero-substituted hydrocarbyl groups, and are preferably those in which the heteroatom, typically —O—, —NH—, or —S—, interrupts a chain of carbon atoms, an example being an alkoxy-alkyl group of 2 to 20 carbons.

$R^3$ is hydrogen or a hydrocarbyl group, which may be derived from a polyolefin, for example polyethylene, polypropylene, polybutylene, or polyisobutylene, or a polyolefin copolymer, for example an ethylene/propylene copolymer. Examples of $R^3$ include dodecyl and octadecyl. Heteroatoms, if present, can again be —O—, —NH—, or —S—. These hydrocarbyl groups preferably have 1 to 20 carbon atoms, more preferably, 1 to 6 carbon atoms.

Either $R^1$ is hydroxyl and $R^2$ and $R^4$ are independently either hydrogen or hydrocarbyl, or $R^2$ and $R^4$ are hydroxyl and $R^1$ is either hydrogen or hydrocarbyl. In one embodiment, $R^1$ is hydrogen, $R^2$ and $R^4$ are hydroxyl, and $R^3$ is either hydrogen or hydrocarbyl in the formula (II) and the calixarene is a resorcinarene. The hydrocarbyl groups preferably have 1 to 24 carbon atoms, more preferably 1 to 12 carbon atoms. The heteroatoms, when present, can be —O—, —NH—, or —S—.

In one embodiment, Y is either sulfur or $(CR^7R^8)_e$, where either one of $R^7$ and $R^8$ is hydrogen and the other is hydrogen or hydrocarbyl; $R^2$ and $R^4$ are independently either hydrogen or hydrocarbyl, $R^3$ is hydrocarbyl; n is 6; and e is at least 1, preferably 1 to 4, more preferably, 1. Preferably, $R^2$ and $R^4$ are hydrogen and $R^3$ is hydrocarbyl, preferably alkyl of greater than 4, more preferably greater than 9, most preferably greater than 12 carbon atoms; and one of $R^7$ or $R^8$ is hydrogen and the other is either hydrogen or alkyl, preferably hydrogen.

The foregoing sulfur-containing calixarenes typically have a molecular weight below 1880. Preferably, the molecular weight of the sulfur-containing calixarene is from 460 to 1870, more preferably from 460 to 1800, most preferably 460 to 1750.

Acids described in U.S. Pat. Nos. 2,933,520; 3,038,935; 3,133,944; 3,471,537; 4,828,733; 5,281,346; 5,336,278;

5,356,546; 5,458,793; and 6,310,011, the disclosures of which are incorporated herein by reference in their entirety, can also be used as the acid compounds of the present invention.

More specifically, such acids include, but are not limited to, compounds of the formula:

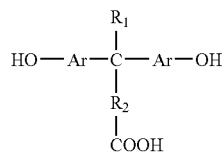

wherein $R_1$ is hydrocarbon or halogen, $R_2$ is hydrocarbon, Ar is substituted or unsubstituted aryl. Useful compounds similar to these include 3,5,3',5'-tetra-substituted 4,4'-dihydroxymethyl carboxylic acids, acids of the formula

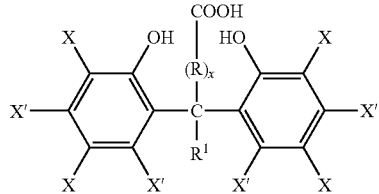

wherein X and X' are independently selected from the group consisting of hydrogen, hydrocarbyl, halogen, R is polymethylene or branched or unbranched alkylene, and x is 0 or 1, i.e., when x is zero, R is absent, and when x is 1, R is present, and $R^1$ is hydrogen or hydrocarbyl.

The acids and salts described in U.S. Pat. Nos. 5,281,346; 5,336,278; 5,356,546; 5,458,793; and 6,310,011 are similar to the above and are also contemplated for use in the practice of the present invention, as are those of the formula

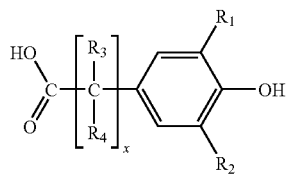

wherein $R_1$ and $R_2$ are hydrogen, hydrocarbyl groups containing 1 to 18 carbon atoms, or tertiary alkyl or aralkyl groups containing 4 to 8 carbon atoms (but both $R_1$ and $R_2$ cannot be hydrogen) $R_3$ and $R_4$ are independently selected from the group consisting of hydrogen, hydrocarbyl groups, aralkyl groups, and cycloalkyl groups, and x=0 to 24.

Oil soluble hydroxy carboxylic acids including, but not limited to, 12-hydroxy stearic acid, alpha hydroxy carboxylic acids and the like can also be employed as the acidic compound of the present invention.

The Basic Organic Compounds

As noted above, the basic organic compound employed in the practice of the present invention is preferably an organic nitrogen base compound, such as an one comprising an N-hydroxy alkyl moiety, preferably an N-hydroxy or N-alkoxy alkyl heterocycle, such as N-hydroxy alkyl imidazolines, N-alkoxy alkyl imidazolines, and N-hydroxy alkyl piperazines. Other heterocyclics that are within the scope of the invention include, but are not limited to, pyrrolidines, piperidines, imidazolidines, pyrazolidines, and derivatives of indole, carbazole, quinoline, and the like. Both water soluble and oil soluble alkanolamines, including polymeric alkanolamines, such as those described in U.S. Pat. No. 3,692,680, can also be used. Such polymeric alkanolamines can be prepared by reacting a suitable amine with an epichlorohydrin compound. U.S. Pat. No. 3,189,652 discloses such a reaction wherein the amine used as a reactant is selected from primary aliphatic amines containing from 12 to 40 carbon atoms and N-aliphatic polyamines including N-alkyl-1,3-diamino-propanes in which the alkyl contains at least 12 carbon atoms and N-aliphatic ethylenediamines, N-aliphatic diaminobutanes, -pentanes, -hexanes, and the like in which the aliphatic group contains from 12 to 40 carbon atoms.

Other organic nitrogen base compounds that are useful in the practice of the present invention include, but are not limited to, those disclosed in U.S. Pat. Nos. 3,446,808; 3,673,186; 3,787,416; the disclosures of which are incorporated herein by reference in their entirety. Such compounds include, for example, N-hydroxyalkyl-piperazines, N-hydroxyalkyl-N'-alkyl piperazines, N-hydroxyalkyl-N'-cycloalkyl-piperazines, N-hydroxyalkyl-N'-alkyl hexahydropyrimidines, N-hydroxyalkyl-N'-cycloalkyl hexahydropyrimidines, N-hydroxyalkyl-N'-alkyl hexahydropyridazines, N-hydroxyalkyl-N'-cycloalkyl hexahydropyridazines, N-hydroxyalkyl-piperidines, N-hydroxyalkyl-N'-alkyl-imidazolidines, N-hydroxyalkyl-N'-cycloalkyl-imidazolidines, N-hydroxyalkyl-pyrrolidine, N-hydroxyalkyl-pyrazolidine, N-hydroxyalkyl-hydrogenated 1,2,3,-triazole, N-hydroxyalkyl-hydrogenated 1,2,4,-triazole, N-hydroxyalkyl-hydrogenated indole, N-hydroxyalkyl-hydrogenated carbazole, N-hydroxyalkyl-hydrogenated quinoline, N-hydroxyalkyl-hydrogenated acridine, N-hydroxyalkyl-hydrogenated phenazine, N-oxyalkyl-N'-hydrocarbyl-saturated cyclic diazines, N-hydroxyalkyl-N'-hydrocarbyl-saturated cyclic diazines, and N-alkoxyalkyl-N'-hydrocarbyl-saturated cyclic diazines, wherein the hydrocarbyl moieties are preferably sec-alkyl or cycloalkyl.

The Boron Compounds

The boron compound can, for example, be boric acid, a trialkyl borate in which the alkyl groups preferably comprise from 1 to 4 carbon atoms each, alkyl boric acid, dialkyl boric acid, boric oxide, boric acid complex, cycloalkyl boric acid, aryl boric acid, dicycloalkyl boric acid, diaryl boric acid, or substitution products of these with alkoxy, alkyl, and/or alkyl groups, and the like. Boric acid is preferred.

The reaction of the boron compound with the acidic and basic compounds of the present invention can be effected in any suitable manner.

In one method the acidic compound and boron compound are refluxed in presence of suitable solvents including naphtha and polar solvents such as water and methanol. After sufficient time the boron compound dissolves whereupon the aminic compound is added slowly to effect neutralization and formation of desired detergent. Diluting oil can be added as needed to control viscosity, particularly during removal of solvents by distillation.

An alcohol, including aliphatic and aromatic alcohols, or a mercaptan, including aliphatic and aromatic mercaptans, can be included in the reaction charge. Preferred aliphatic alcohols include methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, isomers thereof, and the like. Preferred aromatic alcohols include phenol, cresol, xylenol, and the like. The alcohol or aromatic phenol moiety may be substituted with alkoxy groups or thioalkoxy groups. Preferred mercaptans include butyl mercaptan, pentyl mercaptan, hexyl mercaptan, heptyl mercaptan, octyl mercaptan, nonyl mercaptan, decyl mercaptan, undecyl mercaptan, dodecyl mercaptan, and the like, as well as thiophenol, thiocresol, thioxylenol, and the like.

The precise structures of the detergent/anti-oxidant additives of the present invention are not fully understood. However, in one preferred embodiment, in which a $C_{16}$ alkyl salicylic acid was reacted with hydroxyethyl oleic imidazoline (a commercial product) and boric acid, mass spectrometric analysis indicated that the structure of the reaction product was:

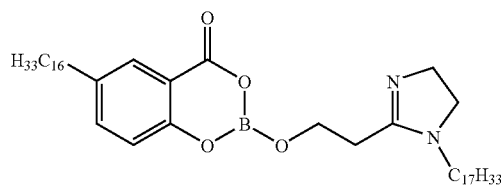

When a $C_{16}$ dialkyl salicylic acid was employed in the reaction, the analysis indicated the following structural formula:

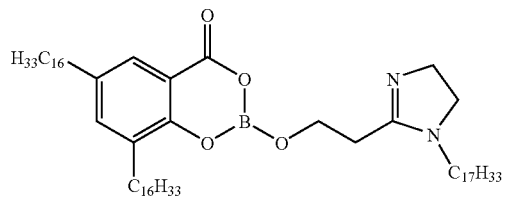

Those skilled in the art will thus understand that the foregoing leads to the following generalized structural formula for this particular aspect of the present invention:

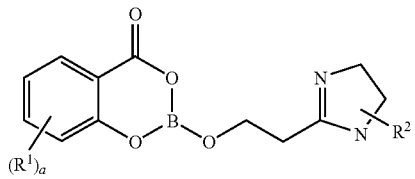

wherein $R^1$ is preferably a hydrocarbyl group, preferably alkyl, of, preferably, from 1 to 50 carbon atoms, more preferably 12 to 30 carbon atoms, most preferably 14 to 18 carbon atoms, a is an integer of 1 or 2 (where a is 2, the $R^1$ groups are independently selected, i.e., they may be the same or different), and $R^2$ is an independently selected hydrocarbyl group, preferably alkyl or alkenyl, preferably of from 1 to 50 carbon atoms, more preferably 12 to 30 carbon atoms, most preferably 14 to 18 carbon atoms.

Clearly, the use of alternative starting materials, as described above, will lead to different, but analogous, structures that are within the scope of the present invention.

The additives of the present invention are especially useful as components in many different lubricating oil and fuel compositions. The additives can be included in a variety of oils with lubricating viscosity including natural and synthetic lubricating oils and mixtures thereof. The additives can be included in crankcase lubricating oils for spark-ignited and compression-ignited internal combustion engines. The compositions can also be used in gas engine lubricants, turbine lubricants, automatic transmission fluids, gear lubricants, compressor lubricants, metal-working lubricants, hydraulic fluids, and other lubricating oil and grease compositions. The additives can also be used in motor fuel compositions.

It is preferred that the compositions of the present invention be included in the oil, fuel, or grease in a concentration in the range of from about 0.01 to about 15 wt %.

Use with Other Additives

The additives of this invention can be used as either a partial or complete replacement for a detergent currently used. They can also be used in combination with other lubricant additives typically found in fuels and motor oils, such as dispersants, anti-wear agents, extreme pressure agents, corrosion/rust inhibitors, antioxidants, anti-foamants, friction modifiers, seal swell agents, demulsifiers, Viscosity Index (VI) improvers, metal passivators, and pour point depressants. See, for example, U.S. Pat. No. 5,498,809 for a description of useful lubricating oil composition additives, the disclosure of which is incorporated herein by reference in its entirety.

Examples of dispersants include polyisobutylene succinimides, polyisobutylene succinate esters, Mannich Base ashless dispersants, and the like. Examples of detergents include neutral and overbased alkali and alkaline earth metal salts of sulfonic acids carboxylic acids, alkyl phenates and alkyl salicylic acids.

Examples of antioxidants include alkylated diphenylamines, N-alkylated phenylenediamines, phenyl-α-naphthylamine, alkylated phenyl-α-naphthylamine, dimethyl quinolines, trimethyldihydroquinolines and oligomeric compositions derived therefrom, hindered phenolics, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds, and the like. The following are exemplary of such additives and are commercially available from Crompton Corporation: Naugalube® 438, Naugalube 438L, Naugalube 640, Naugalube 635, Naugalube 680, Naugalube AMS, Naugalube APAN, Naugard PANA, Naugalube TMQ, Naugalube 531, Naugalube 431, Naugard® BHT, Naugalube 403, and Naugalube 420, among others.

Examples of anti-wear additives that can be used in combination with the additives of the present invention include organo-borates, organo-phosphites, organo-phosphates, organic sulfur-containing compounds, sulfurized olefins, sulfurized fatty acid derivatives (esters), chlorinated paraffins, zinc dialkyldithiophosphates, zinc diaryldithiophosphates, phosphosulfurized hydrocarbons, and the like. The following are exemplary of such additives and are commercially available from The Lubrizol Corporation: Lubrizol 677A, Lubrizol 1095, Lubrizol 1097, Lubrizol 1360, Lubrizol 1395, Lubrizol 5139, and Lubrizol 5604, among others.

Examples of friction modifiers include fatty acid esters and amides, organo molybdenum compounds, molybdenum dialkyldithiocarbamates, molybdenum dialkyl dithiophosphates, molybdenum disulfide, tri-molybdenum cluster dialkyldithiocarbamates, non-sulfur molybdenum compounds and the like. The following are exemplary of such additives and are commercially available from R.T. Vanderbilt Company, Inc.: Molyvan A, Molyvan L, Molyvan 807, Molyvan 856B, Molyvan 822, Molyvan 855, among others. The following are also exemplary of such additives and are commercially available from Asahi Denka Kogyo K. K.: SAKURA-LUBE 100, SAKURA-LUBE 165, SAKURA-LUBE 300, SAKURA-LUBE 310G, SAKURA-LUBE 321, SAKURA-LUBE 474, SAKURA-LUBE 600, SAKURA-LUBE 700, among others. The following are also exemplary of such additives and are commercially available from Akzo Nobel Chemicals GmbH: Ketjen-Ox 77M, Ketjen-Ox 77TS, among others.

An example of an anti-foamant is polysiloxane, and the like. Examples of rust inhibitors are polyoxyalkylene polyol, benzotriazole derivatives, and the like. Examples of VI improvers include olefin copolymers and dispersant olefin copolymers, and the like. An example of a pour point depressant is polymethacrylate, and the like.

Lubricant Compositions

Compositions, when they contain these additives, are typically blended into a base oil in amounts such that the additives therein are effective to provide their normal attendant functions. Representative effective amounts of such additives are illustrated in TABLE 1.

TABLE 1

| Additives | Preferred Weight % | More Preferred Weight % |
|---|---|---|
| V.I. Improver | 1-12 | 1-4 |
| Corrosion Inhibitor | 0.01-3 | 0.01-1.5 |
| Oxidation Inhibitor | 0.01-5 | 0.01-1.5 |
| Dispersant | 0.1-10 | 0.1-5 |
| Lube Oil Flow Improver | 0.01-2 | 0.01-1.5 |
| Detergent/Rust Inhibitor | 0.01-6 | 0.01-3 |
| Pour Point Depressant | 0.01-1.5 | 0.01-0.5 |
| Anti-foaming Agents | 0.001-0.1 | 0.001-0.01 |
| Anti-wear Agents | 0.001-5 | 0.001-1.5 |
| Seal Swell Agents | 0.1-8 | 0.1-4 |
| Friction Modifiers | 0.01-3 | 0.01-1.5 |
| Lubricating Base Oil | Balance | Balance |

When other additives are employed, it may be desirable, although not necessary, to prepare additive concentrates comprising concentrated solutions or dispersions of the subject additives of this invention (in concentrate amounts hereinabove described), together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil can be facilitated by solvents and by mixing accompanied by mild heating, but this is not essential. The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of, typically, from about 2.5 to about 90 percent, preferably from about 15 to about 75 percent, and more preferably from about 25 percent to about 60 percent by weight additives in the appropriate proportions with the remainder being base oil. The final formulations can typically employ about 1 to 20 weight percent of the additive-package with the remainder being base oil.

All of the weight percentages expressed herein (unless otherwise indicated) are based on the active ingredient (AI) content of the additive, and/or upon the total weight of any additive-package, or formulation, which will be the sum of the AI weight of each additive plus the weight of total oil or diluent.

In general, the lubricant compositions of the invention contain the additives in a concentration ranging from about 0.05 to about 30 weight percent. A concentration range for the additives ranging from about 0.1 to about 10 weight percent based on the total weight of the oil composition is preferred. A more preferred concentration range is from about 0.2 to about 5 weight percent. Oil concentrates of the additives can contain from about 1 to about 75 weight percent of the additive reaction product in a carrier or diluent oil of lubricating oil viscosity.

In general, the additives of the present invention are useful in a variety of lubricating oil base stocks. The lubricating oil base stock is any natural or synthetic lubricating oil base stock fraction having a kinematic viscosity at 100° C. of about 2 to about 200 cSt, more preferably about 3 to about 150 cSt, and most preferably about 3 to about 100 cSt. The lubricating oil base stock can be derived from natural lubricating oils, synthetic lubricating oils, or mixtures thereof. Suitable lubricating oil base stocks include base stocks obtained by isomerization of synthetic wax and wax, as well as hydrocracked base stocks produced by hydrocracking (rather than solvent extracting) the aromatic and polar components of the crude. Natural lubricating oils include animal oils, such as lard oil, vegetable oils (e.g., canola oils, castor oils, sunflower oils), petroleum oils, mineral oils, and oils derived from coal or shale.

Many synthetic lubricants are known in the art and these are useful as a base lubricating oil for lubricating compositions containing the subject additives. Surveys of synthetic lubricants are contained in the publications, SYNTHETIC LUBRICANTS by R. C. Gunderson and A. W. Hart, published by Reinhold (N.Y., 1962), LUBRICATION AND LUBRICANTS, E. R. Braithwaite, ed., published by Elsevier Publishing Co., (N.Y., 1967), Chapter 4, pages 166 through 196, "Synthetic Lubricants", and SYNTHETIC LUBRICANTS by M. W. Ranney, published by Noyes Data Corp., (Park Ridge, N.J., 1972). These publications are incorporated herein by reference to establish the state of the art in regard to identifying both general and specific types of synthetic lubricants which can be used in conjunction with the additives of the present invention.

Thus, useful synthetic lubricating base oils include hydrocarbon oils derived from the polymerization or copolymerization of olefins, such as polypropylene, polyisobutylene and propylene-isobutylene copolymers; and the halohydrocarbon oils, such as chlorinated polybutylene. Other useful synthetic base oils include those based upon alkyl benzenes, such as dodecylbenzene, tetra-decylbenzene, and those based upon polyphenyls, such as biphenyls and terphenyls.

Another known class of synthetic oils useful as base oils for the subject lubricant compositions are those based upon alkylene oxide polymers and interpolymers, and those oils obtained by the modification of the terminal hydroxy groups of these polymers, (i.e., by the esterification or etherification of the hydroxy groups). Thus, useful base oils are obtained from polymerized ethylene oxide or propylene oxide or from the copolymers of ethylene oxide and propylene oxide. Useful oils include the alkyl and aryl ethers of the polymerized alkylene oxides, such as methylpolyisopropylene glycol ether, diphenyl ether of polyethylene glycol and diethyl ether of propylene glycol. Another useful series of synthetic base oils is derived from the esterification of the terminal hydroxy group of the polymerized alkylene oxides with mono- or polycarboxylic acids. Exemplary of this series are the acetic acid esters or mixed $C_3$-$C_8$ fatty acid esters of the $C_{13}$ oxo acid diester of tetraethylene glycol.

Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers. Other esters useful as synthetic oils include those made from copolymers of $\alpha$-olefins and dicarboxylic acids which are esterified with short or medium chain length alcohols. The following are exemplary of such additives and are commercially available from Akzo Nobel Chemicals SpA: Ketjenlubes 115, 135, 165, 1300, 2300, 2700, 305, 445, 502, 522, and 6300, among others.

Silicon-based oils, such as the polyalkyl-, polyaryl-, polyalkoxy-, or polyaryloxy-siloxane oils and silicate oils, comprise another useful class of synthetic lubricating oils. Other synthetic lubricating oils include liquid esters of phosphorus-containing acids, polymeric tetrahydrofurans, poly $\alpha$-olefins, and the like.

The lubricating oil may be derived from unrefined, refined, re-refined oils, or mixtures thereof. Unrefined oils are obtained directly from a natural source or synthetic source (e.g., coal, shale, or tar and bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to unrefined oils, except that refined oils have been treated in one or more purification steps to improve one or more properties. Suitable purification techniques include distillation, hydrotreating, dewaxing, solvent extraction, acid or base extraction, filtration, percolation, and the like, all of which are well-known to those skilled in the art. Re-refined oils are obtained by treating refined oils in processes similar to those used to obtain the refined oils. These re-refined oils are also known as reclaimed or reprocessed oils and often are additionally processed by techniques for removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst. Natural waxes are typically the slack waxes recovered by the solvent dewaxing of mineral oils; synthetic waxes are typically the wax produced by the Fischer-Tropsch process. The resulting isomerate product is typically subjected to solvent dewaxing and fractionation to recover various fractions having a specific viscosity range. Wax isomerate is also characterized by possessing very high viscosity indices, generally having a VI of at least 130, preferably at least 135 or higher and, following dewaxing, a pour point of about −20° C. or lower.

The advantages and the important features of the present invention will be more apparent from the following examples.

EXAMPLES

Detergency Performance—Panel Coker Test

The detergency efficacy of crankcase oils can be assessed in terms of deposit forming tendency on a rectangular Al-steel panel in a Panel Coker test. In this test, 200 ml of the test sample is taken in sump and heated at 100° C. For a period of 6 hours, this heated oil is splashed by whiskers on the Al-steel panel, the temperature of which is maintained at 310° C. After completion of the test, any deposits on the panel are weighed. A decrease in the weight of deposits as compared with a similar composition lacking the detergent additive indicates improved detergency.

Antioxidant Performance—Pressure Differential Scanning Calorimetry (PDSC)

PDSC (DuPont Model-910/1090B) can be used for relative antioxidant performance evaluation of the composition. In this method, a test sample (10 mg) taken in a sample boat is subjected to heating from 100-300° C. at the rate of 10° C. per minute under 500 psi oxygen pressure. The onset of oxidation temperature is adopted as a criterion for assessment of antioxidant performance. In general, an increase in onset of oxidation temperature indicates improvement in antioxidant performance. See J. A. Walker and W. Tsang, "Characterization of Lubrication Oils by Differential Scanning Calorimetry", SAE Technical Paper Series, 801383 (Oct. 20-23, 1980).

Example 1

A quantity of 40 grams of alkyl ($C_{14}$-$C_{18}$) salicylic acid was added to a small reaction flask equipped with a mechanical stirrer and a condenser. Fifty grams of naphtha was added along with 40 grams of base oil, 15 grams of water and 30 grams of methanol. Mixing was started, 15 grams of boric acid was added, and then the mixture was heated to 70° C. At that temperature, 48.5 grams of a hydroxy ethyl alkyl imidazoline was added and the reaction temperature was increased slowly to 210° C. to remove volatiles. A clear brown viscous liquid was recovered that had a total alkalinity value of 46. The product was subjected to testing as shown below.

Panel Coker

Five percent of the above product was added to an SAE 50 base oil, mixed, and subjected to the modified panel coker test. At the end of the test, the panel was weighed resulting in 6.5 milligrams of deposits.

Pressure Differential Scanning Calorimetry

The sample of Example 1 was subjected to PDSC testing and found to have an induction time of >180 minutes at 165° C. when the test was stopped.

Example 2

Comparative Example

Example 1 was repeated except that the alkyl imidazoline used was an amino ethyl alkyl imidazoline. The final product was a fluid hazy liquid with poor oil solubility.

Example 3

Comparative Example

Example 1 was repeated but the boric acid was not added. The final product was fluid, bright and clear with very poor panel coker performance producing more than 150 milligrams of carbonaceaous deposit.

Example 4

Comparative Example

In this example, the alkyl salicylic acid of Example 1 was replaced with an alkyl aromatic sulfonic acid. The product recovered was clear, but had extremely poor detergency as measured by 243 milligrams of deposits in panel coker test. The PDSC result was also poor with an induction time of only 34.8 minutes.

Example 5

In this example, the amount of alkyl imidazoline was reduced to close to the theoretical amount of 33 grams required to neutralize the salicylic acid. Excellent detergency was found with panel coker deposits of 3.4 milligrams.

In view of the many changes and modifications that can be made without departing from principles underlying the invention, reference should be made to the appended claims for an understanding of the scope of the protection to be afforded the invention.

What is claimed is:

1. A composition comprising the reaction product of an acidic organic compound, a boron compound, and a basic organic compound, wherein the composition is a metal free detergent and wherein the acidic organic compound is selected from the group consisting of:
   (A) alkyl substituted salicylic acids,
   (B) di-substituted salicylic acids,
   (C) oil soluble hydroxy carboxylic acids,
   (D) salicylic acid calixarenes,
   (E) sulfur-containing calixarenes,
   (F) acids of the formula:

$$HO-Ar-\underset{\underset{COOH}{R_2}}{\overset{R_1}{C}}-Ar-OH$$

wherein $R_1$ is hydrocarbon or halogen, $R_2$ is hydrocarbon, and Ar is substituted or unsubstituted aryl,
   (G) acids of the formula:

[structure with two aryl rings bearing OH and X, X' substituents, connected via C(R)(R¹), with COOH]

wherein X and X' are independently selected from the group consisting of hydrogen, hydrocarbyl, and halogen, R is polymethylene or branched or unbranched alkylene, x is 0 or 1, and $R^1$ is hydrogen or hydrocarbyl,
   (H) acids of the formula:

[structure: HOOC-[C(R_3)(R_4)]_x-aryl ring with R_1, R_2 substituents and OH]

wherein
   $R_1$ and $R_2$ are independently selected from the group consisting of hydrogen, hydrocarbyl groups, tertiary alkyl groups, and tertiary aralkyl groups, provided that both $R_1$ and $R_2$ are not hydrogen,
   $R_3$ and $R_4$ are independently selected from the group consisting of hydrogen, hydrocarbyl groups, aralkyl groups, and cycloalkyl groups, and
   x is from 0 to 24, inclusive; and
   (I) salts of the foregoing acids; and
wherein the basic organic compound is selected from the group consisting of N-hydroxyalkyl-piperazines, N-hydroxyalkyl-N'-alkyl piperazines, N-hydroxyalkyl-N'-cycloakyl-piperazines, N-hydroxyalkyl-N'-alkyl hexahydropyrimidines, N-hydroxyalkyl-N'-cycloalkyl hexahydropyrimidines, N-hydroxyalkyl-N'-alkyl hexahydropyridazines, N-hydroxyalkyl-N'-cycloalkyl hexahydropyridazines, N-hydroxyalkyl-piperidines, N-hydroxyalkyl-N'-alkyl-imidazolidines, N-hydroxyalkyl-N'-cycloalkyl-imidazolidines, N-hydroxyalkyl-pyrrolidine, N-hydroxyalkyl-pyrazolidine, N-hydroxyalkyl-hydrogenated 1,2,3,-triazole, N-hydroxyalkyl-hydrogenated 1,2,4,-triazole, N-hydroxyalkyl-hydrogenated indole, N-hydroxyalkyl-hydrogenated carbazole, N-hydroxyalkyl-hydrogenated guinoline, N-hydroxyalkyl-hydrogenated acridine, N-hydroxyalkyl-hydrogenated phenazine, N-oxyalkyl-N'-hydrocarbyl-saturated cyclic diazines, N-hydroxyalkyl-N'-hydrocarbyl- saturated cyclic diazines, and.

2. The composition of claim 1 wherein the boron compound is selected from the group consisting of boric acid, trialkyl borates, alkyl boric acids, dialkyl boric acids, boric oxide, boric acid complex, cycloalkyl boric acids, aryl boric acids, dicycloalkyl boric acids, diaryl boric acids, and substitution products of the foregoing with alkoxy groups, alkyl groups, alkyl groups, and combinations thereof.

3. The composition of claim 1 wherein the reaction product is

[structure: benzofused dioxaborine with (R¹)_a on aryl ring, B connected via O-CH2CH2- to imidazoline bearing R²]

wherein $R^1$ and $R^2$ are independently selected hydrocarbyl groups, a is an integer of 1 or 2, provided that, where a is 2, the $R^1$ groups are independently selected.

4. The composition of claim 3 wherein the $R^1$ and $R^2$ groups are independently selected hydrocarbyl groups of from 1 to 50 carbon atoms.

* * * * *